US011332469B2

(12) United States Patent
Mittelman et al.

(10) Patent No.: US 11,332,469 B2
(45) Date of Patent: May 17, 2022

(54) SOLID STATE FORMS OF LUMATEPERONE DITOSYLATE SALT

(71) Applicant: ASSIA CHEMICAL INDUSTRIES LTD., Petach Tikva (IL)

(72) Inventors: Ariel Mittelman, Elad (IL); Ido Fuchs, Petah Tikva (IL); Sharona Shachantov, Kfar-Saba (IL); Doron Rudik, Modiin (IL); Rotem Sella-Erez, Tel-Aviv (IL)

(73) Assignee: TEVA PHARMACEUTICALS INTERNATIONAL GMBH, Jona (CH)

( * ) Notice: Subject to any disclaimer, the term of this patent is extended or adjusted under 35 U.S.C. 154(b) by 362 days.

(21) Appl. No.: 16/323,939

(22) PCT Filed: Aug. 8, 2017

(86) PCT No.: PCT/US2017/045877
§ 371 (c)(1),
(2) Date: Feb. 7, 2019

(87) PCT Pub. No.: WO2018/031535
PCT Pub. Date: Feb. 15, 2018

(65) Prior Publication Data
US 2019/0211015 A1 Jul. 11, 2019

Related U.S. Application Data

(60) Provisional application No. 62/486,554, filed on Apr. 18, 2017, provisional application No. 62/400,358, filed on Sep. 27, 2016, provisional application No. 62/382,977, filed on Sep. 2, 2016, provisional application No. 62/382,479, filed on Sep. 1, 2016, provisional application No. 62/372,553, filed on Aug. 9, 2016.

(51) Int. Cl.
*C07D 471/16* (2006.01)
*C07C 309/30* (2006.01)

(52) U.S. Cl.
CPC .......... *C07D 471/16* (2013.01); *C07C 309/30* (2013.01); *C07B 2200/13* (2013.01)

(58) Field of Classification Search
CPC .. C07D 471/16; C07C 309/30; C07B 2200/13
See application file for complete search history.

(56) References Cited

U.S. PATENT DOCUMENTS

| 8,648,077 B2 | 2/2014 | Tomesch et al. |
| 2018/0271862 A1 | 9/2018 | Li et al. |
| 2020/0069683 A1 | 3/2020 | Li et al. |
| 2020/0102309 A1 | 4/2020 | Li et al. |
| 2020/0157100 A1 | 5/2020 | Li |

FOREIGN PATENT DOCUMENTS

| WO | 2008112280 A1 | 9/2008 |
| WO | 2009114181 A2 | 9/2009 |
| WO | 2012071425 A1 | 5/2012 |
| WO | 2017172784 A1 | 10/2017 |
| WO | 2017172811 A1 | 10/2017 |
| WO | 2018175969 A1 | 9/2018 |
| WO | 2019102240 A1 | 5/2019 |
| WO | 2019236889 A1 | 12/2019 |
| WO | 2019241278 A1 | 12/2019 |
| WO | 2020047241 A1 | 3/2020 |
| WO | 2020047407 A1 | 3/2020 |
| WO | 2020047408 A1 | 3/2020 |
| WO | 2020112941 A2 | 6/2020 |

OTHER PUBLICATIONS

Berge, Stephen M. et al., "Review Article: Pharmaceutical Salts", Journal of Pharmaceutical Sciences, vol. 66, No. 1, 1977, p. 1-19, XP055515920.
Byrn, Stephen et al., "Pharmaceutical Solids: A Strategic Approach to Regulatory Considerations", Pharmaceutical Research, vol. 12, No. 7, 1995, p. 945-954, XP055531015.
Cole, P., "ITI-007", Drugs of the Future, vol. 40, No. 10, 2015, p. 643-650, XP055671175.
Gadade, Dipak Dilip et al., "Pharmaceutical Cocrystals: Regulatory and Strategic Aspects, Design and Development", Advanced Pharmaceutical Bulletin, vol. 6, No. 4, 2016, p. 479-494, XP055520634.
Caira, Mino R., "Crystalline polymorphism of Organic Compounds", Topics in Current Chemistry, vol. 198, p. 163-208 (1998).
International Search Report for International Application No. PCT/US2017/045877, International Filing Date Aug. 8, 2017, dated Oct. 18, 2017, 4 pages.
Written Opinion for International Application No. PCT/US2017/045877, International Filing Date Aug. 8, 2017, dated Oct. 18, 2017, 7 pages.
U.S. Appl. No. 17/297,035 "Solid State Forms of Lumateperone Salts and Processes for Preparation of Lumateperone and Salts Thereof" filed on May 26, 2021.

*Primary Examiner* — Joseph R Kosack
(74) *Attorney, Agent, or Firm* — Cantor Colburn LLP

(57) ABSTRACT

Disclosed are solid state forms of lumateperone ditosylate, uses thereof, and pharmaceutical compositions thereof.

33 Claims, 9 Drawing Sheets

SOLID STATE FORMS OF LUMATEPERONE DITOSYLATE SALT

CROSS-REFERENCE TO RELATED APPLICATIONS

This application is a National Stage application of PCT/US2017/045877, filed Aug. 8, 2017, which claims priority to U.S. Provisional Application No. 62/486,554, filed Apr. 18, 2017, U.S. Provisional Application No. 62/400,358, filed Sep. 27, 2016, U.S. Provisional Application No. 62/382,977, filed Sep. 2, 2016, U.S. Provisional Application No. 62/382,479, filed Sep. 1, 2016, and U.S. Provisional Application No. 62/372,553, filed Aug. 9, 2016. The disclosure of each of these applications is incorporated herein by reference in its entirety for all purposes.

FIELD OF THE INVENTION

The present invention encompasses solid state forms of lumateperone ditosylate and pharmaceutical compositions thereof.

BACKGROUND OF THE INVENTION

Lumateperone tosylate has the following formula:

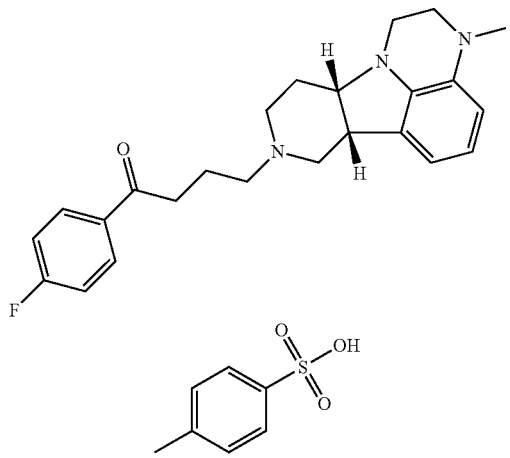

It is under development for the treatment of central nervous system disorders including: schizophrenia, bipolar disorder, depression, sleep and behavioral disturbance in dementia, autism, and other neuropsychiatric disorders.

Lumateperone and its acceptable pharmaceutical salts are described in USRE39,680.

U.S. Pat. No. 8,648,077 describes polymorphs A and B of toluenesulfonic acid addition salt of lumateperone ("lumateperone tosylate").

Polymorphism, the occurrence of different crystalline forms, is a property of some molecules and molecular complexes. A single molecule may give rise to a variety of polymorphs having distinct crystal structures and physical properties like melting point, thermal behaviors (e.g. measured by thermogravimetric analysis—"TGA", or differential scanning calorimetry—"DSC"), X-ray diffraction pattern, infrared absorption fingerprint, and solid state (13C-) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life (chemical/physical stability). For at least these reasons, there is a need for additional solid state forms (including solvated forms) of lumateperone tosylate and other salts thereof for example Lumateperone ditosylate.

SUMMARY OF THE INVENTION

The present invention provides solid state forms of lumateperone ditosylate, and pharmaceutical compositions thereof. These solid state forms can be used to prepare solid state forms of Lumateperone, Lumateperone tosylate, other solid state forms of Lumateperone ditosylate, or other salts and solid state forms thereof.

The present invention also encompasses the use of the solid state forms of lumateperone ditosylate of the present invention for the preparation of pharmaceutical compositions and/or formulations of lumateperone ditosylate.

The present disclosure provides solid state forms of Lumateperone ditosylate for use in the preparation of pharmaceutical compositions and/or formulations comprising Lumateperone ditosylate.

The present invention comprises a process for preparing the above mentioned pharmaceutical compositions and/or formulations. The process comprises combining the lumateperone ditosylate solid state form with at least one pharmaceutically acceptable excipient.

The solid state forms and the pharmaceutical compositions and/or formulations of lumateperone ditosylate of the present invention can be used as medicaments, particularly for the treatment of disorders of the central nervous system.

DETAILED DESCRIPTION OF THE INVENTION

Figure 1:
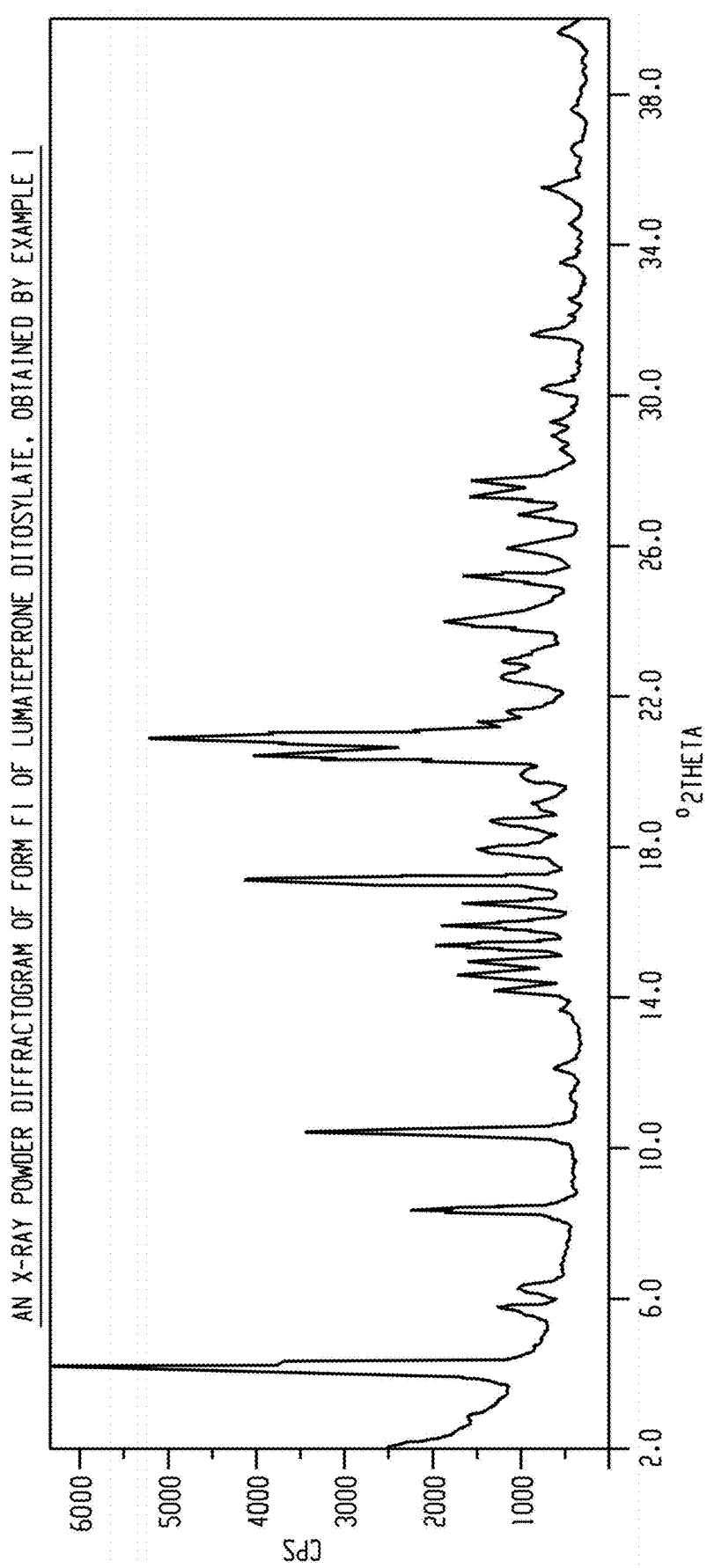
FIG. 1 shows an X-ray powder diffractogram of form F1 of lumateperone ditosylate, obtained by example 1.

The present invention encompasses solid state forms of lumateperone ditosylate. and pharmaceutical compositions thereof. These solid state forms can be used to prepare solid state forms of Lumateperone, lumateperone tosylate, other solid state forms of Lumateperone ditosylate, or other salts and solid state forms thereof.

Solid state properties of lumateperone ditosylate can be influenced by controlling the conditions under which the lumateperone ditosylate is obtained in solid form.

In some embodiments, the crystalline form of lumateperone ditosylate of the invention is substantially free of any other forms of lumateperone tosylate/ditosylate, or of specified polymorphic forms of lumateperone tosylate/ditosylate, respectively.

As used herein, the term lumateperone tosylate (or lumateperone tosylate salt) refers to 4-((6bR,10aS)-3-methyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone monotosylate salt.

As used herein, the term lumateperone ditosylate (or lumateperone ditosylate salt) refers to 4-((6bR,10aS)-3-methyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone ditosylate salt.

A solid state form (or polymorph) may be referred to herein as polymorphically pure or as substantially free of any other solid state (or polymorphic) forms. As used herein in this context, the expression "substantially free of any other forms" will be understood to mean that the solid state form contains 20% or less, 10% or less, 5% or less, 2% or less, or 1% or less of any other forms of the subject compound as measured, for example, by XRPD. Thus, a solid state of lumateperone ditosylate described herein as substantially free of any other solid state forms would be understood to contain greater than 80% (w/w), greater than 90% (w/w), greater than 95% (w/w), greater than 98% (w/w), or greater than 99% (w/w) of the subject solid state form of lumateperone tosylate or lumateperone ditosylate. Accordingly, in some embodiments of the invention, the described solid state forms of lumateperone ditosylate may contain from 1% to 20% (w/w), from 5% to 20% (w/w), or from 5% to 10% (w/w) of one or more other solid state forms of lumateperone tosylate or lumateperone ditosylate.

As used herein, the term chemically pure refers to a material which is substantially free of chemical impurities, such as reaction by-products, un-reacted intermediates or degradation product. The term "substantially free" means that the chemically pure material of the present invention contains 3% (w/w) or less of chemical impurities. According to some embodiments, the chemically pure material of the present invention contains 3% (w/w) or less, 2% (w/w) or less, 1% (w/w) or less, 0.5% (w/w) or less, or 0.2% (w/w) or less of chemical impurities. In other embodiments, chemically pure material of the present invention contains from 0.01% to 3% (w/w), of chemical impurities.

Depending on which other solid state forms comparison is made with, the solid state forms of lumateperone ditosylate of the present invention have advantageous properties selected from at least one of the following: chemical purity, flowability, solubility, dissolution rate, morphology or crystal habit, stability-such as chemical stability as well as thermal and mechanical stability with respect to polymorphic conversion, stability towards dehydration and/or storage stability, low content of residual solvent, a lower degree of hygroscopicity, and advantageous processing and handling characteristics such as compressibility, and bulk density.

A solid state form, such as a crystal form or amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Lumateperone ditosylate referred to herein as being characterized by graphical data "as depicted in" or "as substantially depicted in" a Figure will thus be understood to include any crystal forms of Lumateperone ditosylate characterized with the graphical data having such small variations, as are well known to the skilled person, in comparison with the Figure.

As used herein, the term "isolated" in reference to a solid state form of lumateperone ditosylate of the present invention corresponds to a solid state form of lumateperone ditosylate that is physically separated from the reaction mixture in which it is formed.

As used herein, unless stated otherwise, the XRPD measurements are taken using copper Kα radiation wavelength 1.5418 Å.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or a crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, typically about 16 hours.

As used herein, the term "reduced pressure" refers to a pressure that is less than atmospheric pressure. For example, reduced pressure is about 10 mbar to about 50 mbar.

As used herein, and unless stated otherwise, the term "anhydrous" in relation to crystalline lumateperone ditosylate relates to a crystalline lumateperone ditosylate which does not include any crystalline water (or other solvents) in a defined, stoichiometric amount within the crystal. Moreover, an "anhydrous" form does not contain more than 1% (w/w) of either water or organic solvents as measured for example by TGA.

As used herein crystalline form A of Lumateperone Tosylate refers to a crystalline form which may be characterized by X-ray powder diffraction pattern as disclosed in U.S. Pat. No. 8,648,077.

In one embodiment, the present invention comprises a crystalline form of lumateperone ditosylate, designated form F1, characterized by data selected from one or more of the following: an X-ray powder diffraction pattern having peaks at: 4.2, 6.3, 10.4, 14.6 and 18.7 degrees two theta±0.2 degrees two theta; an X-ray powder diffraction pattern substantially as depicted in FIG. 1; and combinations of these data.

Figure 2:
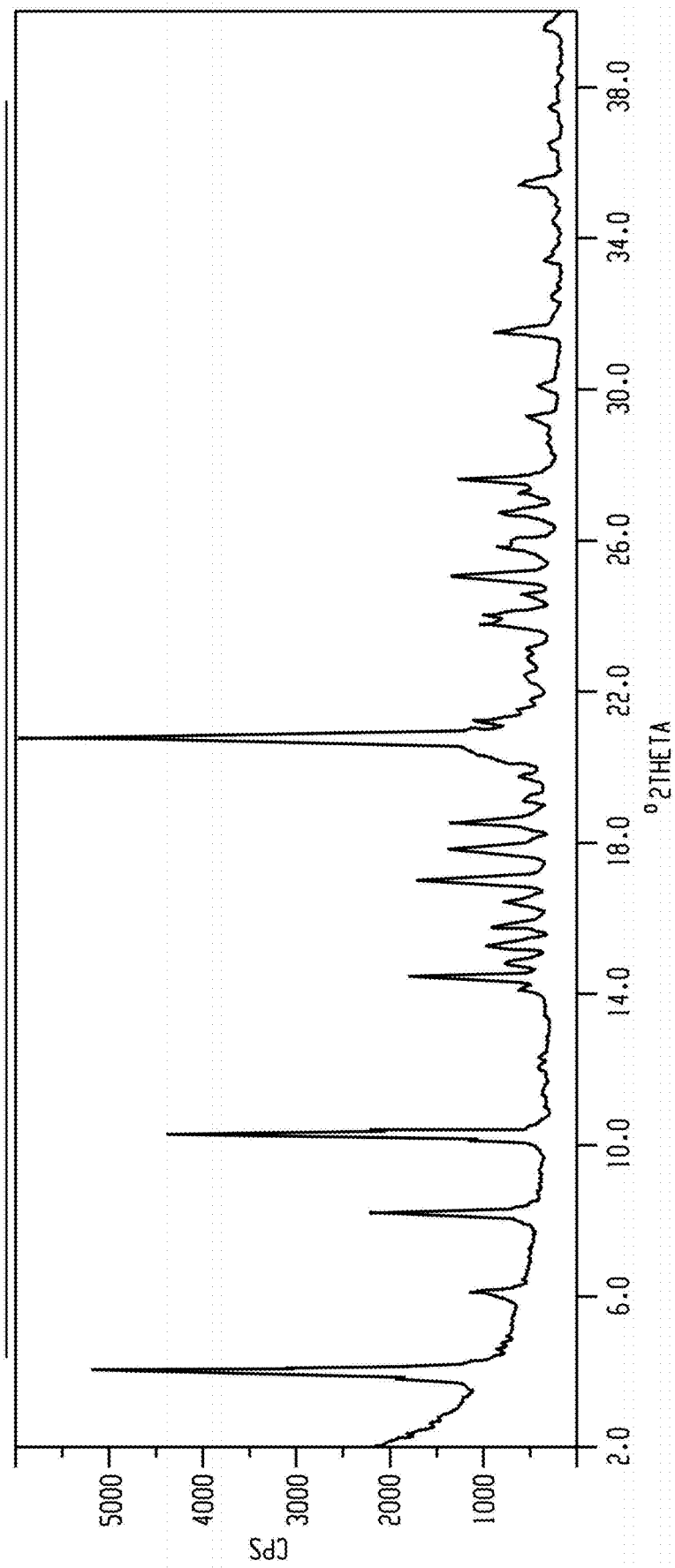
FIG. 2 shows an X-ray powder diffraction pattern of form F1 of lumateperone ditosylate, obtained by example 2.

Alternatively, crystalline form F1 of Lumateperone ditosylate may be characterized by data selected from one or more of the following: an X-ray powder diffraction pattern having peaks at: 4.2, 6.3, 10.4, 14.6 and 18.7 degrees two theta±0.2 degrees two theta; an X-ray powder diffraction pattern substantially as depicted in FIG. 2; and combinations of these data.

Figure 8:
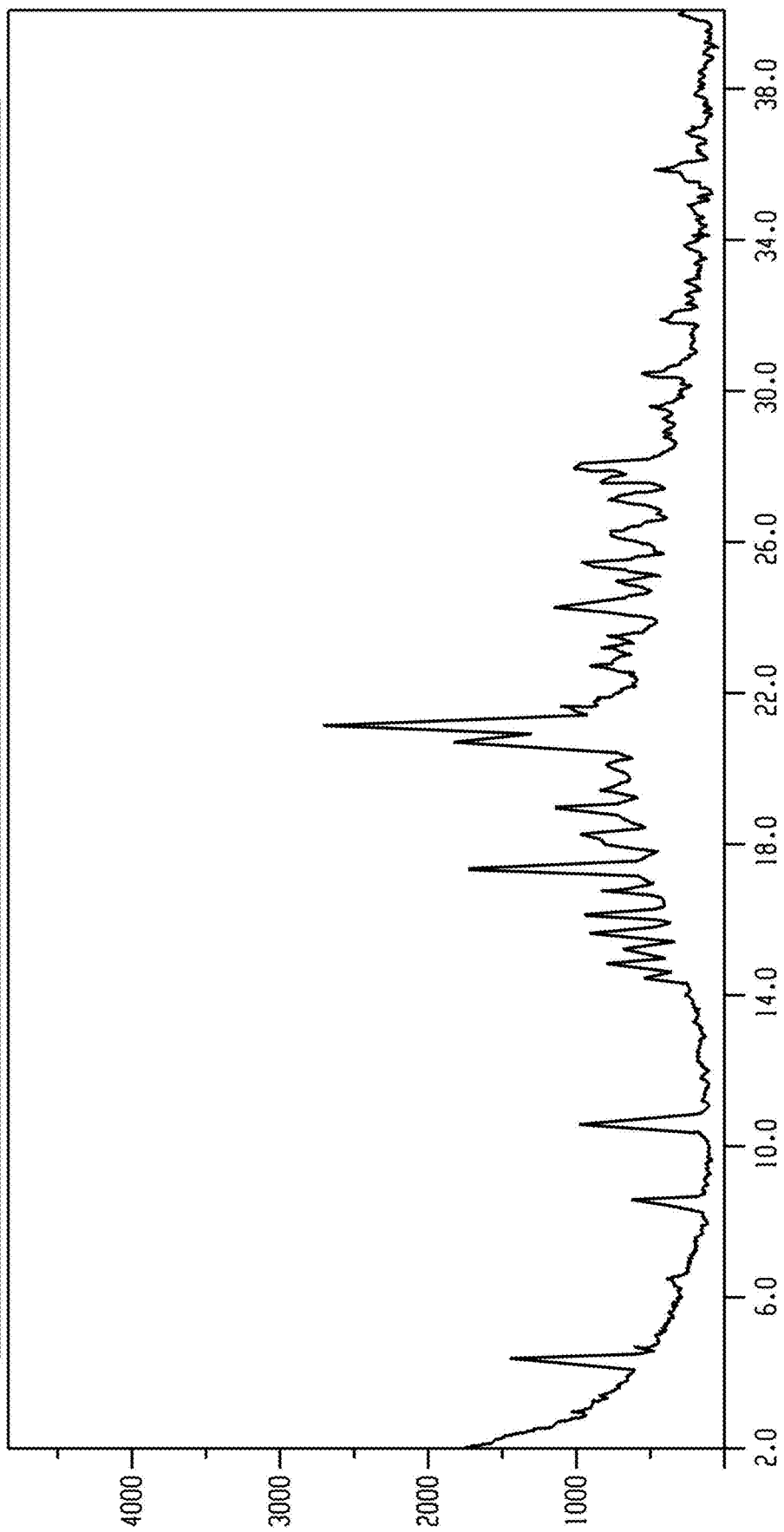
FIG. 8 shows an X-ray powder diffraction pattern of form F1 of lumateperone ditosylate, obtained by example 5.
Figure 9:
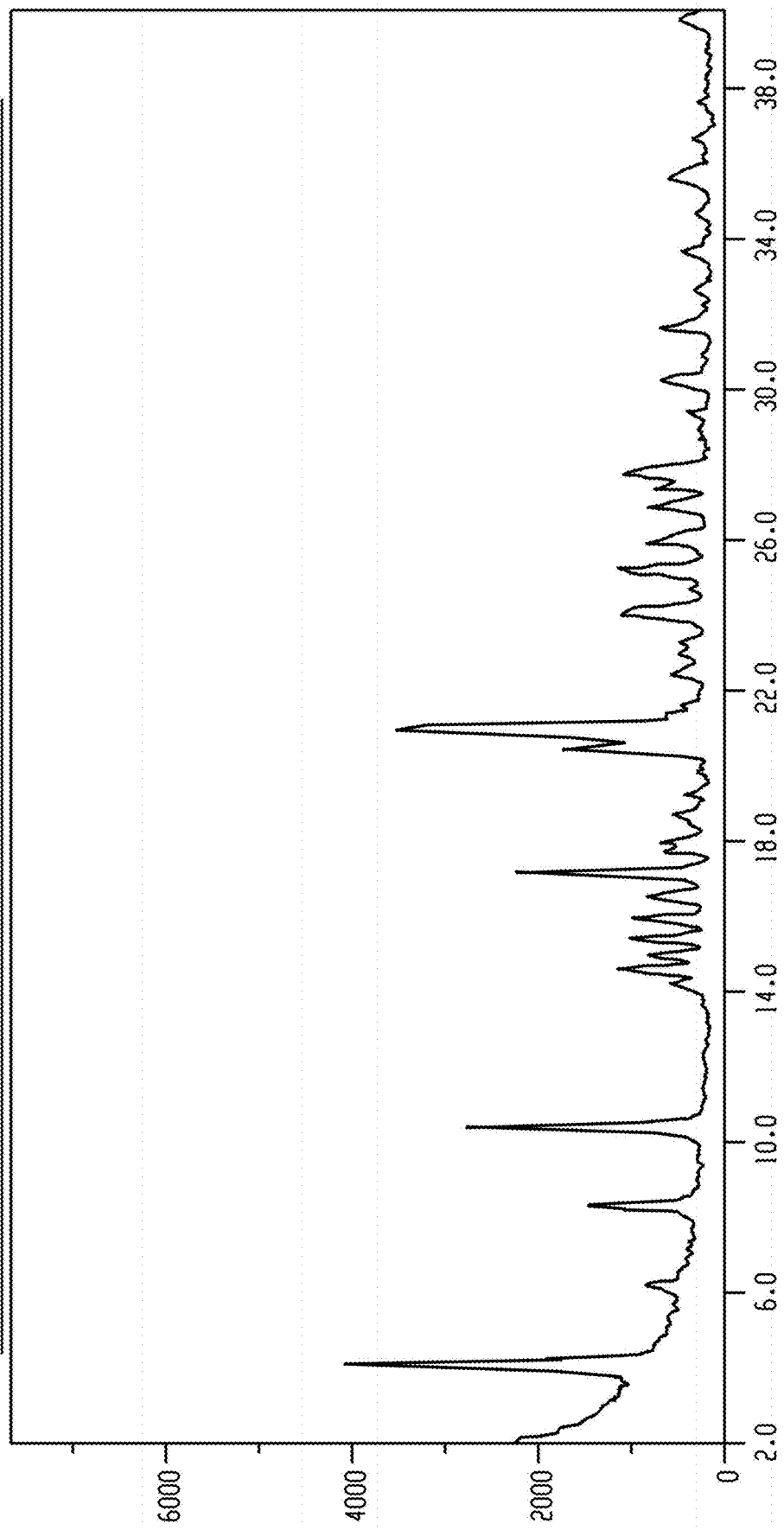
FIG. 9 shows an X-ray powder diffraction pattern of form F1 of lumateperone ditosylate, obtained by example 8.

Alternatively, crystalline form F1 of Lumateperone ditosylate may be characterized by data selected from one or more of the following: an X-ray powder diffraction pattern having peaks at: 4.2, 6.3, 10.4, 14.6 and 18.7 degrees two theta±0.2 degrees two theta, and an X-ray powder diffraction pattern substantially as depicted in FIG. 8 or FIG. 9. Crystalline form F1 of Lumateperone ditosylate may be characterized by an X-ray powder diffraction pattern having peaks at: 4.2, 6.3, 10.4, 14.6 and 18.7 degrees two theta±0.2 degrees two theta, in combination with an X-ray powder diffraction pattern substantially as depicted in either of FIG. 8 or FIG. 9.

Figure 4:
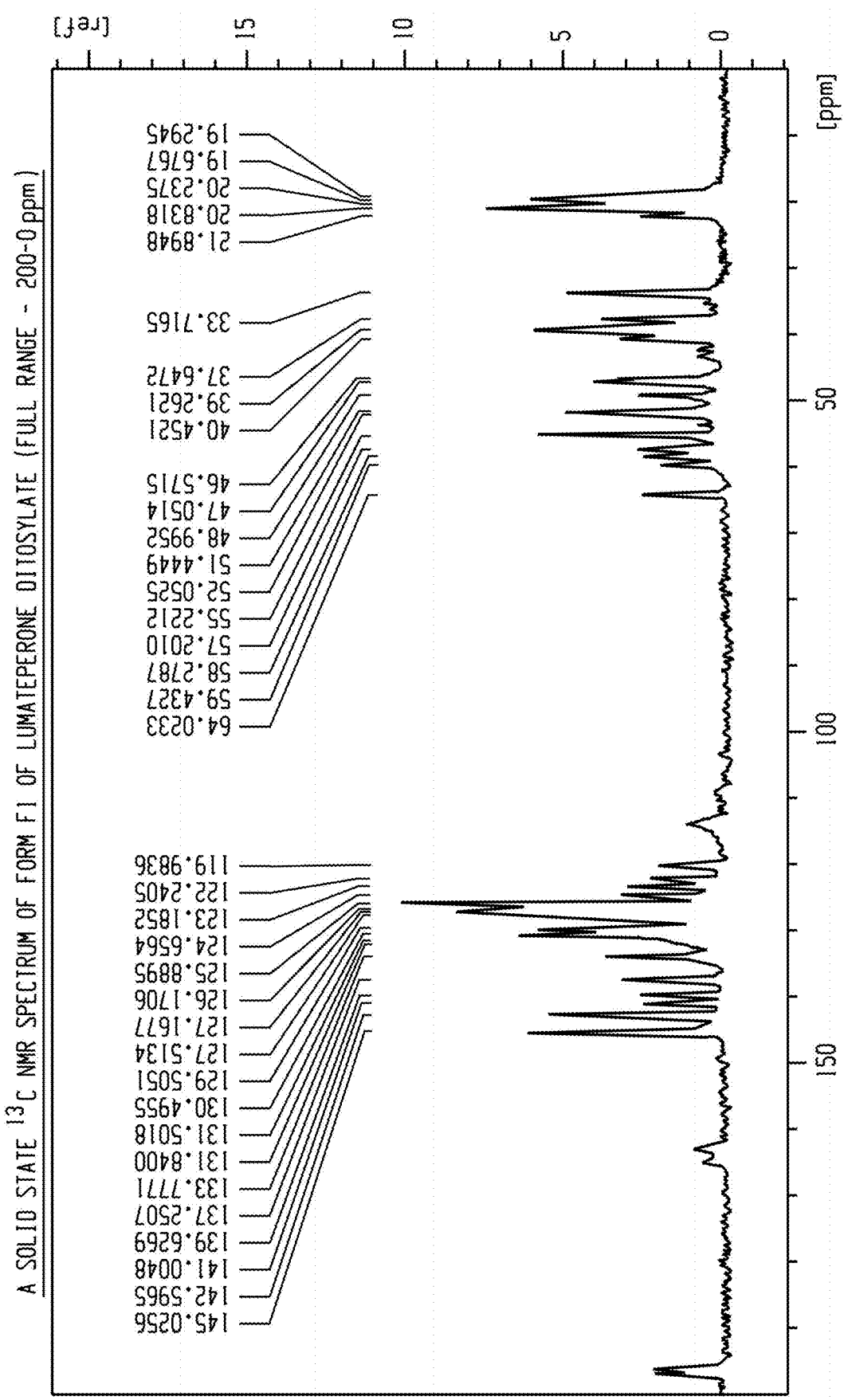
FIG. 4 shows a solid state $^{13}$C NMR spectrum of Form F1 of Lumateperone ditosylate (Full range-200-0 ppm).
Figure 5:
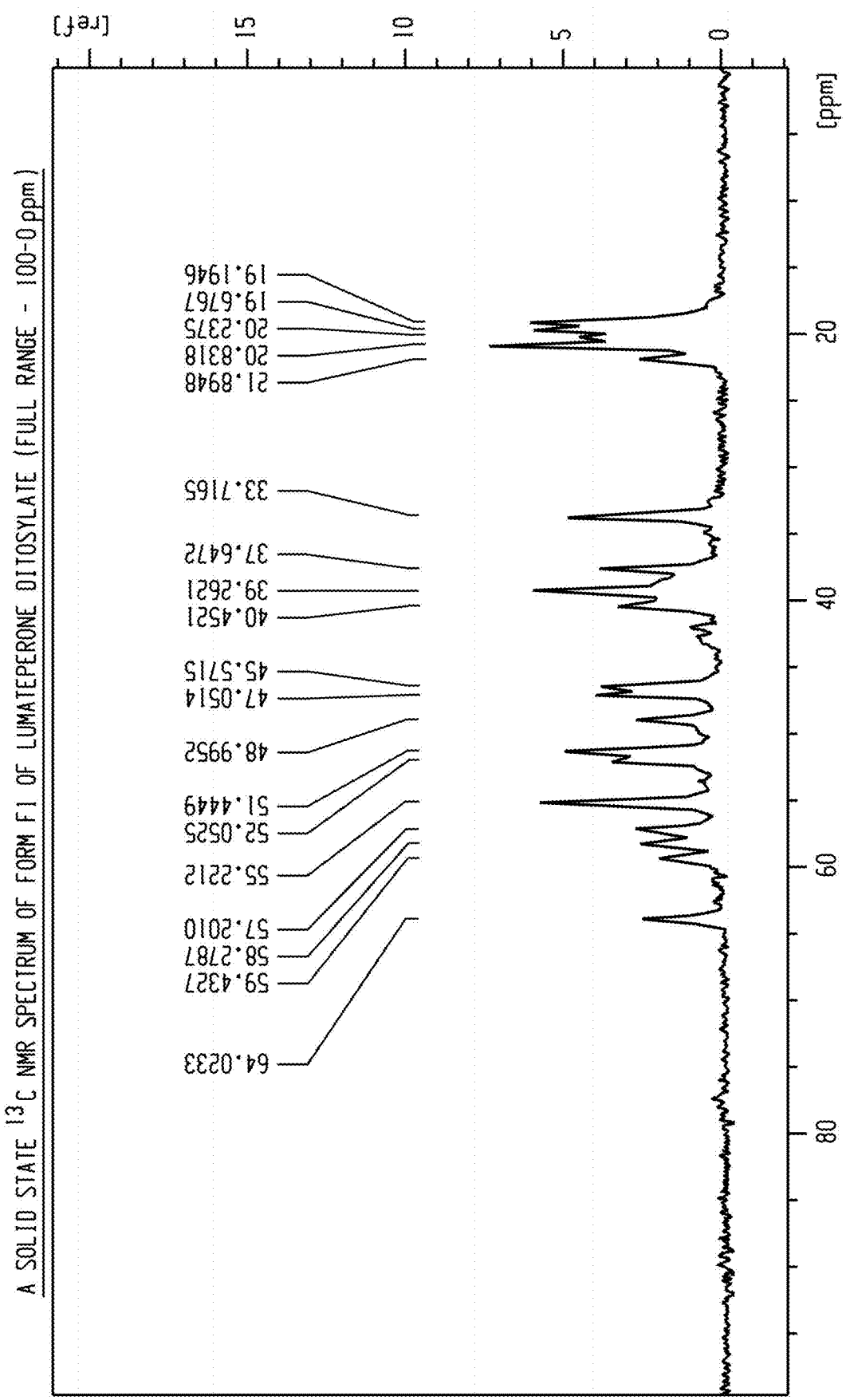
FIG. 5 shows a solid state $^{13}$C NMR spectrum of Form F1 of Lumateperone ditosylate (Full range-100-0 ppm).
Figure 6:
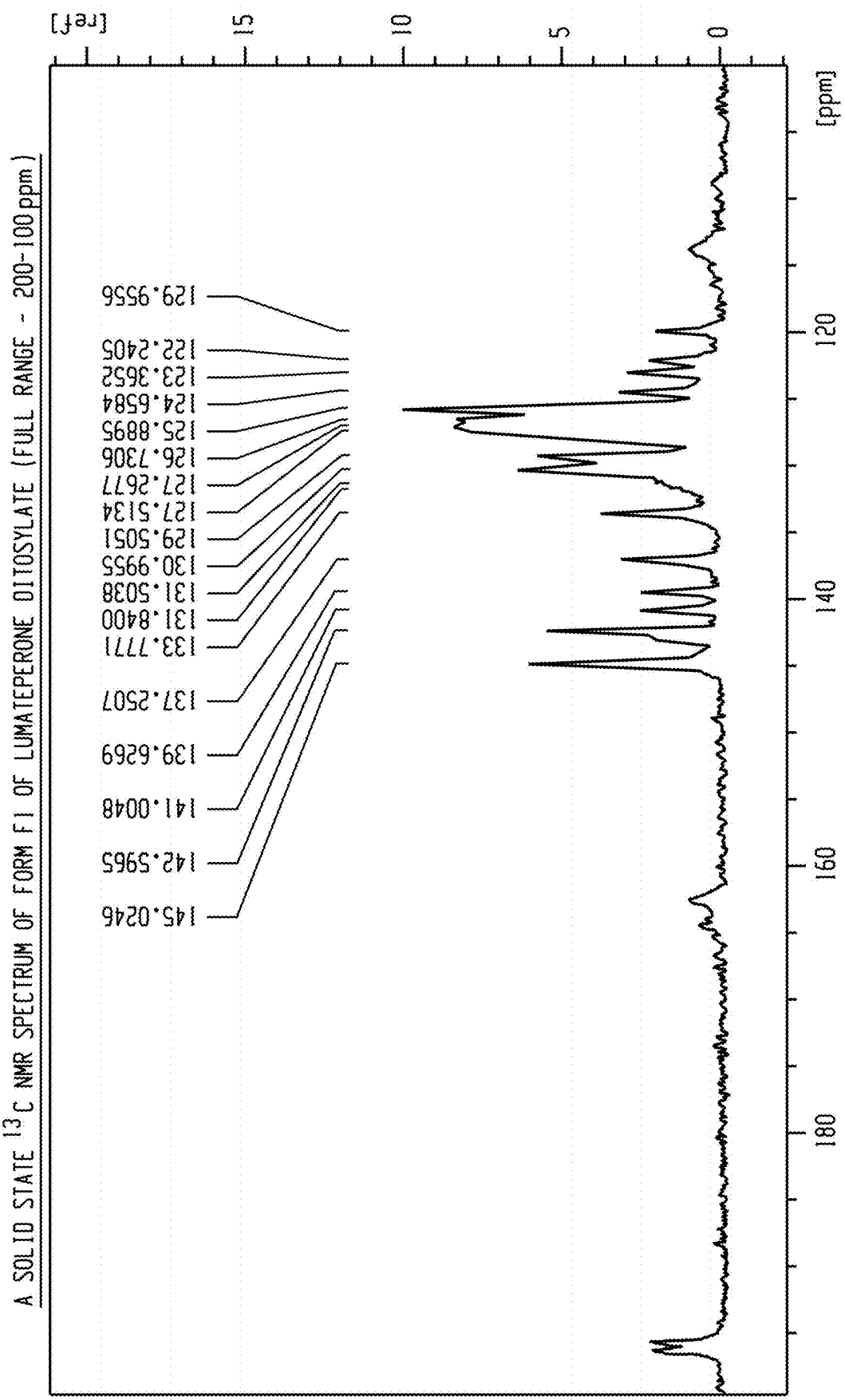
FIG. 6 shows a solid state $^{13}$C NMR spectrum of Form F1 of Lumateperone ditosylate (Full range-200-100 ppm).
Figure 7:
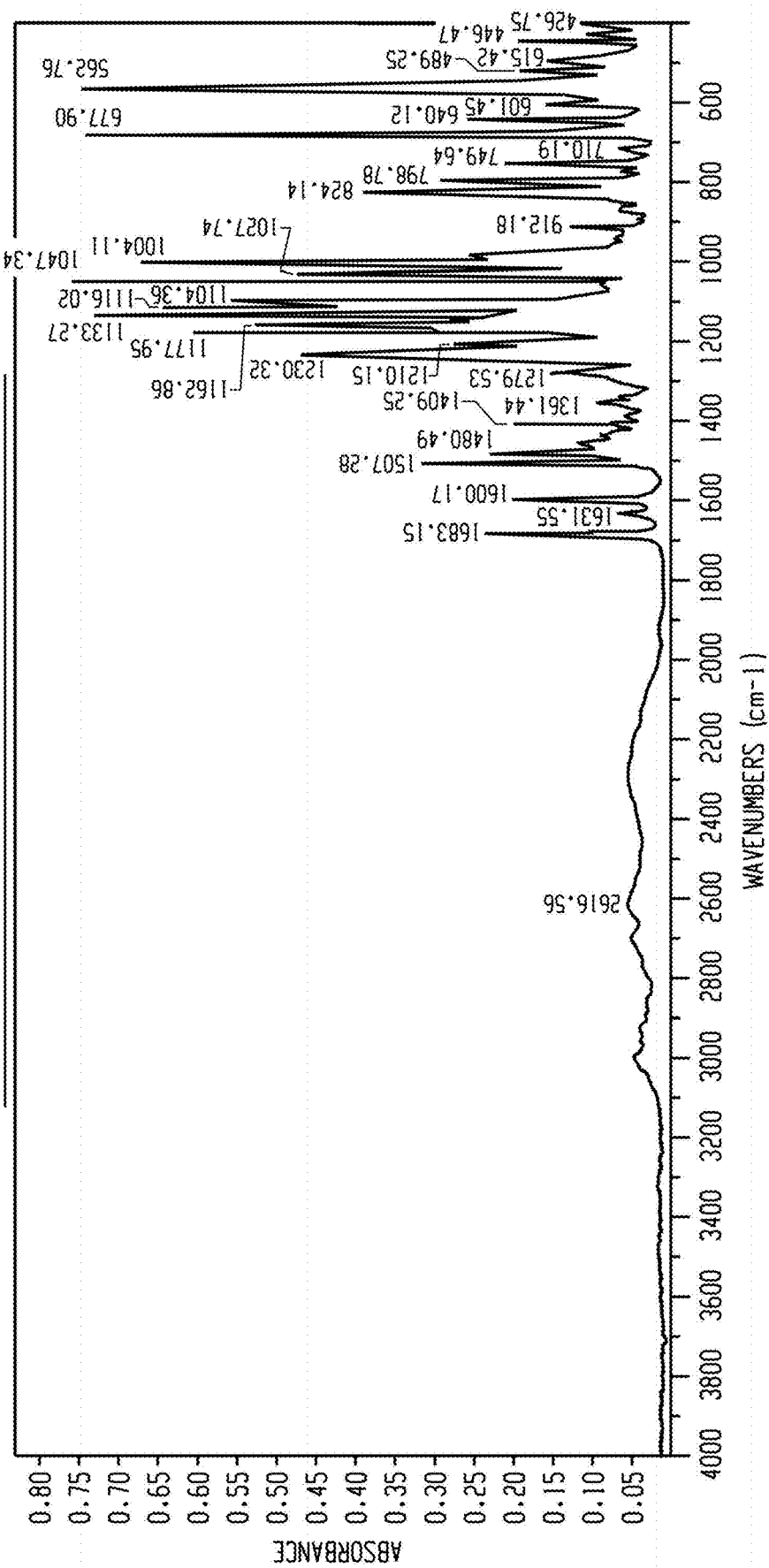
FIG. 7 shows an FTIR spectrum of Form F1 of Lumateperone ditosylate.

In some embodiments, crystalline form F1 of lumateperone ditosylate may be characterized by a solid state $^{13}$C NMR spectrum having peaks at 142.6, 141.0, 133.8, 129.5 and 123.2 ppm±0.2 ppm; a solid state $^{13}$C NMR spectrum having peaks at 142.6, 141.0, 133.8, 129.5 and 123.2 ppm±0.2 ppm and also by the absence of one, two, three or four peaks selected from: 194.5, 110.2, 62.2 and 35.7 ppm±0.2 ppm; a solid state $^{13}$C NMR spectrum having the following chemical shift absolute differences from a reference peak at 64.0 ppm±2 ppm of 78.6, 77.0, 69.8, 65.5 and 59.2 ppm±0.1 ppm; a solid state $^{13}$C NMR spectrum substantially as depicted in FIG. 4, 5 or 6; an FT-IR spectrum having absorptions at 2617, 1632, 1480, 1280, 1210, 1163, 1104, 1004, 824, 750 cm$^{-1}$±2 cm$^{-1}$; and combinations of these data.

In some embodiments, crystalline form F1 of lumateperone ditosylate may be characterized by X-ray powder diffraction pattern having peaks at: 4.2, 6.3, 10.4, 14.6 and 18.7 degrees two theta±0.2 degrees two theta and also having one, two, three, four or five peaks selected from: 15.4, 20.4, 21.3, 24.0 and 25.1 degrees two theta±0.2 degrees two theta; and combinations of these data.

Crystalline form F1 of lumateperone ditosylate may be further characterized by the XRPD pattern having peaks at: 4.2, 6.3, 10.4, 14.6 and 18.7 degrees two theta±0.2 degrees two theta; and also by the absence of one, two, three or four peaks selected from: 11.4, 13.4, 17.5 and 23.5 degrees two theta±0.2 degrees two theta.

Alternatively, crystalline form F1 of lumateperone ditosylate may be further characterized by the XRPD pattern having peaks at: 4.2, 6.3, 10.4, 14.6 and 18.7 degrees two theta±0.2 degrees two theta; and also by the absence of a peak at 5.7 degrees two theta±0.2 degrees two theta.

Preferably the crystalline form F1 as defined in any aspect or embodiment of the invention as disclosed herein is additionally characterized by an absence of a XRPD peak at 5.7 degrees two theta±0.2 degrees two theta.

By the absence of one or more peaks at x, y or z+/−0.2 deg. 2-theta, it is understood that there is no distinct peak at the specified position, in particularly when taking into account any "noise" in the XRPD spectrum. The skilled person would readily be able to determine the absence or presence of an XRPD peak at a given position.

Crystalline form F1 of lumateperone ditosylate may be characterized by the data set forth in the following table.

TABLE 1

X-ray powder diffraction peaks of F1 of lumateperone ditosylate.
peak position (degrees two theta ± 0.2 degrees two theta)

| |
|---|
| 4.2 |
| 6.3 |
| 8.4 |
| 10.4 |
| 14.2 |
| 14.6 |
| 14.9 |
| 15.4 |
| 15.9 |
| 16.5 |
| 17.1 |
| 17.9 |
| 18.7 |
| 19.3 |
| 19.8 |
| 20.4 |
| 22.5 |
| 23.0 |
| 23.2 |
| 24.0 |
| 25.1 |
| 25.9 |
| 26.8 |
| 27.3 |
| 27.7 |
| 29.3 |
| 30.2 |
| 33.5 |
| 35.5 |

In some embodiments crystalline form F1 of lumateperone ditosylate may be anhydrous.

Crystalline form F1 of lumateperone ditosylate may be characterized by each of the above characteristics alone and/or by all possible combinations.

In one embodiment of the present disclosure, form F1 of Lumateperone ditosylate is isolated.

In another embodiment of the present disclosure, form F1 of Lumateperone ditosylate is polymorphically pure.

In a particular embodiment of the present disclosure, F1 of Lumateperone ditosylate is substantially free of any other form of Lumateperone tosylate/ditosylate, or of specified polymorphic forms of Lumateperone tosylate/ditosylate.

In another particular embodiment of the present disclosure, F1 of Lumateperone ditosylate is substantially free of form A of Lumateperone tosylate.

Particularly, crystalline form F1 of Lumateperone ditosylate contains: less than 20%, less than 10 wt %, less than 5 wt %, less than 2 wt %, less than 1 wt %, of Form A of Lumateperone tosylate, as measured by XRPD. Accordingly, the content of crystalline form A of Lumateperone tosylate in crystalline form F1 of Lumateperone ditosylate can be quantified by measuring characteristic peak(s) of form A. Suitable characteristic peaks of crystalline form A that may be used for the above described measurement are at: 5.7, 11.4 and/or 13.4 degrees two theta±0.2 degrees two theta.

Figure 3:
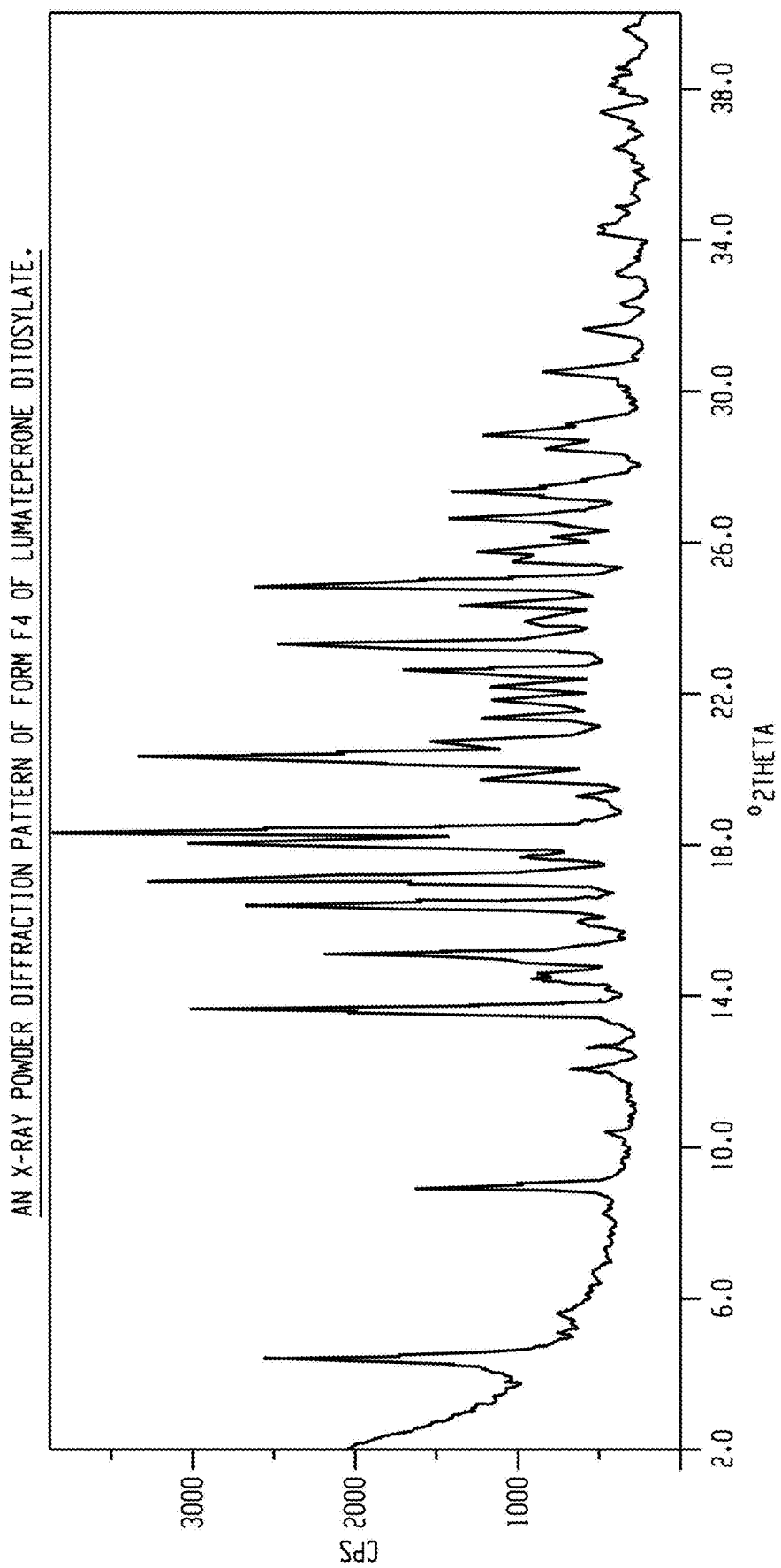
FIG. 3 shows an X-ray powder diffraction pattern of form F4 of Lumateperone ditosylate.

The present disclosure comprises a crystalline form of Lumateperone ditosylate, designated form F4. The crystalline form F4 of Lumateperone ditosylate may be characterized by data selected from one or more of the following: an X-ray powder diffraction pattern substantially as depicted in FIG. 3; an X-ray powder diffraction pattern having peaks at 4.5, 9.0, 12.7, 13.7 and 22.2 degrees two theta±0.2 degrees two theta; and combinations of these data.

In some embodiments, crystalline form F4 of lumateperone ditosylate may be characterized by X-ray powder diffraction pattern having peaks at: 4.5, 9.0, 12.7, 13.7 and 22.2 degrees two theta±0.2 degrees two theta and also having one, two, three, four or five peaks selected from: 15.1, 18.0, 18.3, 20.4 and 24.8 degrees two theta±0.2 degrees two theta; and combinations of these data.

Crystalline form F4 of lumateperone ditosylate may be characterized by each of the above characteristics alone and/or by all possible combinations.

In one embodiment of the present disclosure, form F4 of Lumateperone ditosylate is isolated.

In another aspect the present disclosure provides processes for preparation of crystalline forms of Lumateperone ditosylate. In one embodiment the present disclosure provides a process for preparing crystalline form F1 of Lumateperone ditosylate, preferably wherein form F1 is substantially free of any other form of Lumateperone tosylate/ditosylate, more preferably form F1 is substantially free of form A Lumateperone tosylate comprising:
  a) providing:
    i) a mixture of Lumateperone and at least about 2 equivalents of p-toluenesulfonic acid; or
    ii) a mixture of Lumateperone monotosylate and at least about 1 equivalent of p-toluene sulfonic acid;
    optionally wherein the mixture of (i) or (ii) is provided in a solvent system which optionally comprises water;
  and carrying out one or more of the following steps (b)-(f), wherein steps (b), (c), (d) and/or (e) can be carried out in any order:
    b) stirring
    c) cooling
    d) concentrating and/or
    e) adding an antisolvent, and
    f) optionally isolating Lumateperone ditosylate form F1.
  The mixture in step a may be a solution or a suspension/slurry.

Steps (b), (c), (d) and (e) can be carried out in any order, for example, i.e. the cooling step may be performed before or after the concentration, or the addition of an anti-solvent may be carried out before cooling.

In one embodiment the mixture in step (a) is a solution. The solvent system in step (a) comprises one or more of ethers, preferably $C_3$-$C_8$ ethers, cyclic ethers, preferably $C_4$ to $C_{10}$ cyclic ethers, ketones, preferably $C_3$-$C_8$ ketones, alcohols preferably $C_1$-$C_4$ alcohols, esters (preferably $C_3$-$C_8$ esters), preferably alkyl acetates (particularly $C_2$-$C_7$ alkyl acetates) or mixtures thereof. More preferably the solvent system comprises one or more of methanol, ethanol, THF, 1,4-dioxane, methyl ethyl ketone.

The solution obtained in step (a) can be filtered, if desired, to dispose of foreign particles, while maintaining the filtered solution and filtrate at almost the same temperature.

Preferably the process of the present invention is performed with stirring. Suitable anti-solvents for step (d) include but are not limited to ethers, preferably aliphatic ether, more preferably $C_4$-$C_8$ ethers, alkanes, preferably C3-C8 alkanes, and cycloalkanes, preferably $C_5$-$C_{10}$ cycloalkanes, preferably the anti-solvent is MTBE or heptane.

In some embodiments, crystallization of form F1 may be afforded without addition of anti-solvent, for example by cooling the reaction mixture.

In another embodiment the mixture in step a is a suspension/slurry, suitable organic solvents for step (a) include but are not limited to ethers, preferably $C_3$-$C_8$ ethers, cyclic ethers, preferably $C_4$ to $C_{10}$ cyclic ethers, ketones, preferably $C_3$-$C_8$ ketones, alcohols preferably $C_1$-$C_4$ alcohols, esters (preferably $C_3$-$C_8$ esters), preferably alkyl acetates (particularly $C_2$-$C_7$ alkyl acetates), alkanes, preferably $C_3$-$C_8$ alkanes, and cycloalkanes, preferably $C_5$-$C_{10}$ cycloalkanes, or mixtures thereof.

Preferably the process of the present invention is performed with stirring. In any one of the above described processes crystalline form F1 can be isolated by any method known in the art, For example, crystalline form F1 of Lumateperone ditosylate can be separated by filtering the slurry or decanting the solvent from the slurry. The isolating method can further comprise washing and drying steps.

Preferred processes comprise:

A. Providing a mixture (ii) of Lumateperone monotosylate and at least about 1 equivalent of p-toluene sulfonic acid in a solvent mixture comprising two organic solvents, and stirring the mixture for a suitable period of time (preferably about 0.5 to about 30 hours, about 1 to about 15 hours, about 3 to about 10 hours, or about 5 to about 8 hours) and isolating the crystalline Form F1 lumateperone ditosylate, wherein the stirring may be conducted at about 5 to about 45° C., preferably about 10 to about 40° C., or about 18 to about 28° C. Preferred solvent mixtures include an ether, ester, ketone and/or alcohol as described above (particularly an ether, and more particularly 1,4-dioxane) and in combination with an alkane as described above (preferably heptane);

B. Providing a mixture (ii) of Lumateperone monotosylate and at least about 1 equivalent of p-toluene sulfonic acid in a solvent mixture comprising two organic solvents, and stirring the mixture for a suitable period of time (preferably about 0.5 to about 30 hours, about 1 to about 15 hours, about 3 to about 10 hours, or about 5 to about 8 hours) and isolating the crystalline Form F1 lumateperone ditosylate, wherein the stirring may be conducted at about −10 to about 15° C., preferably about −5 to about 10° C., or about 0 to about 5° C. Preferred solvent mixtures include a ketone and/or alcohol as described above (particularly a ketone, and more particularly; methyl ethyl ketone; or an alcohol as described above, particularly ethanol) in combination with an alkane as described above (preferably n-heptane);

C. Providing a mixture (i) of Lumateperone and at least about 2 equivalents of p-toluenesulfonic acid, in at least one solvent (preferably an alcohol, and more preferably methanol) to form a solution, stirring the mixture for a suitable period of time (preferably about 0.5 to about 30 hours, about 1 to about 15 hours, about 3 to about 10 hours, or about 5 to about 8 hours), concentrating, and optionally triturating with a suitable solvent (e.g. an ether, particularly MTBE), and isolating the crystalline Form F1 lumateperone ditosylate, wherein the stirring may be conducted at about −10 to about 25° C., preferably about −5 to about 15° C., or about 0 to about 10° C.

D. Providing a mixture (ii) of Lumateperone monotosylate and at least about 1 equivalent of p-toluene sulfonic acid in a solvent, optionally heating, and stirring the mixture for a suitable period of time (preferably about 0.25 to about 10 hours, about 0.5 to about 10 hours, or about 5 to about 8 hours) and isolating the crystalline Form F1 lumateperone ditosylate, wherein the stirring may be conducted at about −10 to about 25° C., preferably about −5 to about 15° C., or about 0 to about 10° C. Preferred solvents include ketones or ethers and more particularly; methyl ethyl ketone or 1,4-dioxane. Prior to stirring, the mixture may optionally be heated (e.g. to about 40 to about 100° C., preferably about 60 to about 80° C.;

E. Providing a mixture (ii) of Lumateperone monotosylate and at least about 1 equivalent of p-toluene sulfonic acid in a solvent (preferably an ketone as described above, and more preferably methyl ethyl ketone), adding an antisolvent (preferably a hydrocarbon, and more preferably heptane), stirring the mixture for a suitable period of time (0.5 to about 30 hours, about 1 to about 15 hours, about 3 to about 10 hours, or about 3 to about 8 hours and isolating the crystalline Form F1 lumateperone ditosylate, wherein the stirring may be conducted at about −10 to about 25° C., preferably about −5 to about 15° C., or about 0 to about 10° C.

Preferably, in any process of the present invention as described herein, the p-toluenesulfonic acid is used in the form of the monohydrate.

Preferably in any process of the present invention, the mixture of Lumateperone and at least about 2 equivalents of p-toluenesulfonic acid; or the mixture of Lumateperone monotosylate and at least about 1 equivalent of p-toluene sulfonic acid is prepared by portionwise (e.g. dropwise) addition of p-toluene sulfonic acid to the Lumateperone. Preferably, the portionwise addition is conducted with stirring.

In another aspect the disclosure encompasses to solid state forms of Lumateperone ditosylate produced by any of the processes as disclosed herein.

The present invention encompasses a process for preparing other Lumateperone salts or solid state forms. The process comprises converting any one of the Lumateperone ditosylate solid state forms provided in the present disclosure to said other Lumateperone salts. The conversion can be done, for example, by a process comprising basifying any one or a combination of the above described Lumateperone ditosylate forms and reacting the obtained Lumateperone base with an appropriate acid, to obtain the corresponding salt. Alternatively, the conversion can be done by salt switching, i.e., reacting a Lumateperone acid addition salt, with an acid having a $pK_a$ which is lower than the $pK_a$ of the acid of the first Lumateperone acid addition salt. For example reacting Lumateperone ditosylate with an acid having a $pK_a$ which is lower than the $pK_a$ of p-Toluene Sulfonic acid.

Thus, any of the processes described herein may further comprise converting the Lumateperone ditosylate to another salt or solid state form by basifying and reacting with an appropriate acid, or by salt switching as indicated above. The process may further comprise combining the resulting salt or solid state form with at least one pharmaceutically acceptable excipient to prepare a pharmaceutical composition or formulation.

The above described solid state forms of lumateperone ditosylate can be used to prepare chemically pure lumateperone ditosylate, Lumateperone tosylate and/or other salts of Lumateperone. In certain embodiments, the present invention encompasses the above described solid state forms of lumateperone ditosylate for use in the chemical purification of lumateperone ditosylate, lumateperone tosylate, Lumateperone and/or other salts of Lumateperone.

The above described solid state forms of lumateperone ditosylate can be used to prepare pharmaceutical compositions and/or formulations. In certain embodiments, the present invention encompasses the above described solid state forms of lumateperone ditosylate for use in the preparation of pharmaceutical compositions and/or formulations.

Thus, any of the processes described herein may further comprise combining the Lumateperone ditosylate with at least one pharmaceutically acceptable excipient to prepare a pharmaceutical composition or formulation.

The present invention also comprises pharmaceutical compositions and formulations comprising the above described solid state forms of lumateperone ditosylate. Typically, the pharmaceutical composition is a solid composition and the lumateperone ditosylate retains its solid state form.

The pharmaceutical compositions and/or formulations can be prepared by a process comprising combining any one or a combination of the above-described solid state forms of lumateperone ditosylate with at least one pharmaceutically acceptable excipient.

The present disclosure comprises processes for preparing a pharmaceutical composition comprising Lumateperone ditosylate. The processes comprise combining a Lumateperone ditosylate solid state forms with at least one pharmaceutically acceptable excipient.

The solid state forms of lumateperone ditosylate of the present invention can also be used as a medicament, particularly for the treatment of disorders of the central nervous system.

The present invention further encompasses 1) the use of any of the above-described solid state forms of lumateperone ditosylate in the manufacture of a pharmaceutical composition, and 2) a method of treating a subject suffering from disorders of the central nervous system including: schizophrenia, bipolar disorder, depression, sleep and behavioral disturbance in dementia, autism, and other neuropsychiatric disorders, or otherwise in need of the treatment, comprising administration of an effective amount of a pharmaceutical composition comprising one or more of the solid state forms of lumateperone ditosylate described herein.

Having thus described the invention with reference to particular preferred embodiments and illustrative examples, those in the art can appreciate modifications to the invention as described and illustrated that do not depart from the spirit and scope of the invention as disclosed in the specification. The Examples are set forth to aid in understanding the invention but are not intended to, and should not be construed to limit its scope in any way.

X-Ray Powder Diffraction Method:

The analysis was performed on an ARL (SCINTAG) powder X-Ray diffractometer model X'TRA equipped with a solid state detector. Copper-Kα radiation of 1.5418 Å was used. Scanning parameters: range: 2-40 degrees two-theta; scan mode: continuous scan; step size: 0.05°, and a rate of 3 deg/min.

$^{13}$C Solid-State NMR Method $^{13}$C SSNMR was performed at 125 MHz using Bruker Avance II+ 500

SB probe using 4 mm rotors

Magic angle was set using KBr

Homogeneity of magnetic field checked using adamantane

Parameters for Cross polarization optimized using glycine

Spectral reference set according to glycine as external standard (176.03 ppm for low field carboxyl signal)

Scanning parameters:

Magic Angle Spinning Rate: 11 kHz; Delay time: 3 sec.; Number of Scans: 2048 scans; Temperature: 0° C.

FT-IR Spectroscopy

Thermo FT-IR Spectrometer Nicolet.

The samples were studied in ATR mode.

The spectrum was scanned between 4000-400 $cm^{-1}$.

All the spectra were measured in 16 scans.

Resolution: 4.0 $cm^{-1}$.

EXAMPLES

Lumateperone can be prepared according to any method known in the art, for example according to WO2008/112280.

Lumateperone tosylate can be prepared according to any method known in the art (e.g., WO2009/114181). Form A of Lumateperone tosylate can be prepared according to WO2009/114181.

Example 1: Preparation Procedure of Lumateperone Ditosylate Form F1

Lumateperone tosylate (0.3 gr) was charged to glass vial containing magnetic stirrer rod and deionized water (5 ml) at room temperature. To the slurry, Na$_2$CO$_3$ (0.063 gr in 5 ml water) was added and the obtained reaction mixture was stirred overnight at room temperature. The obtained material was decanted from the water and dissolved completely in dichloromethane. MgSO$_4$ was added to the solution followed by filtration and evaporation.

The obtained material was then mixed with THF (7 vol; 1.4 mL) and p-toluenesulfonic acid monohydrate (0.156 gr) was added at 2° C., followed by the addition of heptane (2 ml). The slurry was set to mix overnight, followed by filtration and washing with heptane. The filtrated solid was then characterized by X-ray powder diffraction to give lumateperone ditosylate form F1 as depicted in FIG. 1.

Example 2: Preparation Procedure of Lumateperone Ditosylate Form F1

Lumateperone PTSA salt (1.008 g) was charged to glass reactor with stirrer rod and 15 mL of deionized water at room temperature. To the slurry, a Na$_2$CO$_3$ (0.191 g) solution in 15 mL water was introduced and mixed overnight at room temperature. The solid material was separated from water by decantation and dissolved in dichloromethane (until clear solution was achieved). MgSO$_4$ was added to the solution for water extraction followed by filtration and evaporation of the clear dichloromethane solution.

0.135 g of the resulting material was then dissolved in methyl ethyl ketone (1.4 mL) and 0.069 g of p-toluenesulfonic acid monohydrate followed by addition of 2 mL heptane at 2° C. under N$_2$ inlet. The slurry was set to mix overnight, followed by filtration and washing by heptane and drying at 35° C. in vacuum oven. The resulting solid was then characterized by X-ray powder diffraction to give Lumateperone ditosylate form F1 as depicted in FIG. 2.

Example 3: Preparation Procedure of Lumateperone Ditosylate Form F4

Lumateperone tosylate salt (3.112 g) was charged to a glass reactor with mechanical stirrer rod and 75 mL of deionized water at room temperature, followed by Na$_2$CO$_3$ addition (0.708 g). The achieved slurry was then mixed overnight at room temperature. The water was decanted from the resulting material, which was later dissolved completely in dichloromethane (70 mL) followed by 20×3 mL wash in water and drying over MgSO$_4$. The resulting clear solution was then filtrated and evaporated in rotovap to give viscous solid. 0.316 g of the resulting material was then mixed with 3.5 mL 2-propanol (IPA) to give a white slurry. To this slurry p-toluenesulfonic acid monohydrate (PTSA (MH)) was added (0.164 g) and mixed at 15° C. for 3 h. The resulting slurry was filtered and washed with IPA and heptane. The filtrated solid was then characterized by X-ray powder diffraction to give Lumateperone ditosylate form F4 as depicted in FIG. 3.

Example 4: Preparation Procedure of Lumateperone Ditosylate Form F1

Lumateperone monotosylate form A (255 mg, 1 eq) was mixed with p-toluenesulfonic acid monohydrate (186 mg, 2.17 eq) in 6 mL of 1,4-dioxane/Heptane (1:1 ratio). Mixture was stirred overnight at ambient conditions followed by filtration. The gray solid obtained was characterized by X-ray powder as Lumateperone ditosylate form F1.

Example 5: Preparation Procedure of Lumateperone Ditosylate Form F1

Lumateperone monotosylate form A (325 mg, 1 eq) was mixed with p-toluenesulfonic acid monohydrate (247 mg, 2.26 eq) in 7 mL of methyl ethyl ketone (MEK)/Heptane (1:1 ratio). The mixture was stirred overnight at 2° C. under N$_2$ atmosphere, filtered and washed with heptane. The resulting solid was characterized by X-ray powder diffraction to give Lumateperone ditosylate form F1 as depicted in FIG. 8.

Example 6: Preparation Procedure of Lumateperone Ditosylate Form F1

Lumateperone monotosylate form A (255 mg, 1 eq) was mixed with p-toluenesulfonic acid monohydrate (172 mg, 2 eq) in 7 mL of Ethanol/Heptane (1:1 ratio). The mixture was stirred overnight at 2° C. under N$_2$ atmosphere followed by filtration. The solid obtained was characterized by X-ray powder as Lumateperone ditosylate form F1.

Example 7: Preparation Procedure of Lumateperone Ditosylate Form F1

Lumateperone free base (716 mg, 1 eq) and p-toluenesulfonic acid monohydrate (773 mg, 2.2 eq) were mixed in methanol (10V) at RT to give clear solution. The solution was stirred at 5° C. overnight and then the solvent was evaporated. MTBE (5 vol) was added to the residue at RT to give a precipitation. The mixture was stirred for 2 hours at RT, the solid was filtered and identified by X-ray powder diffraction as Lumateperone ditosylate form F1.

Example 8: Preparation Procedure of Lumateperone Ditosylate Form F1

Lumateperone monotosylate form A (262 mg, 1 eq) was dissolved in 1.3 mL methyl ethyl ketone (MEK) and a solution of p-toluenesulfonic acid monohydrate (100 mg, 1.134 eq) in 1.3 mL MEK was added. The mixture was stirred at 25° C. for 1 hour, cooled to 5° C. and stirred overnight. The resulting solid was characterized by X-ray powder diffraction to give Lumateperone ditosylate form F1 as depicted in FIG. 9.

Example 9: Preparation Procedure of Lumateperone Ditosylate Form F1

Lumateperone monotosylate form A (243 mg, 1 eq) was dissolved in 1.2 mL 1,4-dioxane and a solution of p-toluenesulfonic acid monohydrate (106 mg, 1.296 eq) in 1.2 mL 1,4-dioxane was added. The mixture was heated to 70° C. for 1 hour, cooled to 5° C. and stirred overnight. The solid was filtered and characterized by X-ray powder as Lumateperone ditosylate form F1.

Example 10: Preparation Procedure of Lumateperone Ditosylate Form F1

To a stirred mixture of Lumateperone monotosylate form A (1.95 g, 1 eq), p-toluenesulfonic acid monohydrate (680 mg, 1.034 eq) and 30 mL MEK under $N_2$ atmosphere, Heptane (30 mL) was added. The mixture was stirred for 5 hours at 2° C. and the solid was filtered, washed with heptane and characterized by X-ray powder as Lumateperone ditosylate form F1.

The invention claimed is:

1. A solid state form of Lumateperone ditosylate, selected from:
  (A) a crystalline form of Lumateperone ditosylate designated form F1, characterized by data selected from one or more of the following:
    (i) an XRPD pattern having peaks at: 4.2, 6.3, 10.4, 14.6 and 18.7 degrees two theta ±0.2 degrees two theta; and also by the absence of two, three or four peaks selected from: 11.4, 13.4, 17.5 and 23.5 degrees two theta ±0.2 degrees two theta;
    (ii) an XRPD pattern having peaks at: 4.2, 6.3, 10.4, 14.6 and 18.7 degrees two theta ±0.2 degrees two theta; and also by the absence of a peak at 5.7 degrees two theta ±0.2 degrees two theta;
    (iii) an X-ray powder diffraction pattern substantially as depicted in FIG. 2, 8, or 9;
    (iv) a solid state $^{13}C$ NMR spectrum having peaks at 142.6, 141.0, 133.8, 129.5 and 123.2 ppm ±0.2 ppm and also by the absence of one, two three or four peaks selected from: 194.5, 110.2, 62.2 and 35.7 ppm ±0.2 ppm; and
    (v) a solid state $^{13}C$ NMR spectrum substantially as depicted in FIG. 4, 5, or 6; or
  (B) a crystalline form of Lumateperone ditosylate designated form F1, which is substantially free of any other solid state or polymorphic forms, which is characterized by data selected from one or more of the following:
    (i) an X-ray powder diffraction pattern having peaks at: 4.2, 6.3, 10.4, 14.6 and 18.7 degrees two theta ±0.2 degrees two theta;
    (ii) an XRPD pattern having peaks at: 4.2, 6.3, 10.4, 14.6 and 18.7 degrees two theta ±0.2 degrees two theta and also having one, two, three, four or five peaks selected from: 15.4, 20.4, 21.3, 24.0 and 25.1 degrees two theta ±0.2 degrees two theta;
    (iii) a solid state $^{13}C$ NMR spectrum having peaks at 142.6, 141.0, 133.8, 129.5 and 123.2 ppm ±0.2 ppm; and
    (iv) a solid state $^{13}C$ NMR spectrum having the following chemical shift absolute differences from a reference peak at 64.0 ppm ±2 ppm of 78.6, 77.0, 69.8, 65.5 and 59.2 ppm ±0.1 ppm.

2. The crystalline form F1 of Lumateperone ditosylate according to claim 1(A) further characterized by one or more of the following:
  (i) an X-ray powder diffraction pattern having peaks at: 4.2, 6.3, 10.4, 14.6 and 18.7 degrees two theta ±0.2 degrees two theta and also having one, two, three, four or five peaks selected from: 15.4, 20.4, 21.3, 24.0 and 25.1 degrees two theta ±0.2 degrees two theta;
  (ii) a solid state $^{13}C$ NMR spectrum having the following chemical shift absolute differences from a reference peak at 64.0 ppm ±2 ppm of 78.6, 77.0, 69.8, 65.5 and 59.2 ppm ±0.1 ppm.

3. The crystalline form F1 of Lumateperone ditosylate according to claim 1 further characterized by an FT-IR spectrum having absorptions at 2617, 1632, 1480, 1280, 1210, 1163, 1104, 1004, 824, 750 cm'±2 cm'.

4. The crystalline form F1 according to claim 1(A), wherein the crystalline form is substantially free of any other solid state forms.

5. The crystalline form F1 according to claim 1, wherein the crystalline form is isolated.

6. A process for preparing crystalline form F1 of Lumateperone ditosylate, comprising:
  a) providing:
    i) a mixture of Lumateperone and at least about 2 equivalents of p-toluenesulfonic acid; or
    ii) a mixture of Lumateperone monotosylate and at least about 1 equivalent of p-toluene sulfonic acid;
    optionally wherein the mixture of (i) or (ii) is provided in a solvent system which optionally comprises water;
  and carrying out one or more of the following steps (b)-(f) wherein steps (b), (c), (d) and (e) can be carried out in any order:
  b) stirring
  c) cooling
  d) concentrating and/or
  e) adding an antisolvent, and
  f) optionally isolating Lumateperone ditosylate form F1.

7. The process according to claim 6 wherein the mixture in step (a) is a solution.

8. The process according to claim 6, wherein the solvent system in step (a) comprises one or more of ethers, ketones, alcohols, esters, or mixtures thereof.

9. The process according to claim 8 wherein the solvent system in step (a) comprises one or more of methanol, ethanol, THF, 1,4-dioxane, or methyl ethyl ketone.

10. The process according to claim 6, wherein the antisolvent in step (e) is selected from the group consisting of ethers, alkanes, and cycloalkanes.

11. A process according to claim 6, comprising:
   (A) providing a mixture of Lumateperone monotosylate and at least about 1 equivalent of p-toluene sulfonic acid in a solvent mixture comprising two organic solvents, stirring the mixture about 0.5 to about 30 hours, and isolating the crystalline Form F1 lumateperone ditosylate, wherein the stirring is conducted at about 5 to about 45° C., and wherein the solvent mixture comprises an ether, ester, ketone and/or alcohol in combination with an alkane or cycloalkane;
   (B) providing a mixture of Lumateperone monotosylate and at least about 1 equivalent of p-toluene sulfonic acid in a solvent mixture comprising two organic solvents, stirring the mixture for about 0.5 to about 30 hours, and isolating the crystalline Form F1 lumateperone ditosylate, wherein the stirring is conducted at about −10 to about 15° C., and wherein the solvent mixture comprises a ketone and/or alcohol; methyl ethyl ketone; or an alcohol in combination with an alkane or cycloalkane (preferably n heptane);
   (C) providing a mixture of Lumateperone and at least about 2 equivalents of p-toluenesulfonic acid, in at least one solvent to form a solution, stirring the mixture for about 0.5 to about 30 hours, concentrating, optionally triturating with a suitable solvent and isolating the crystalline Form F1 lumateperone ditosylate, wherein the stirring is conducted at about −10 to about 25° C.;
   (D) providing a mixture of Lumateperone monotosylate and at least about 1 equivalent of p-toluene sulfonic acid in a solvent, optionally heating stirring the mixture for about 0.25 to about 10 hours, and isolating the crystalline Form F1 lumateperone ditosylate, wherein the stirring is conducted at about −10 to about 25° C., wherein the solvent comprises a ketone or ether; or
   (E) providing a mixture of Lumateperone monotosylate and at least about 1 equivalent of p-toluene sulfonic acid in a solvent, adding an antisolvent, stirring the mixture for a about 0.5 to about 30 hours, and isolating the crystalline Form F1 lumateperone ditosylate, wherein the stirring is conducted at about −10 to about 25° C.

12. A process according to claim 6, wherein the p-toluenesulfonic acid is used in the form of the monohydrate.

13. A process according to claim 6, wherein the mixture of Lumateperone and at least about 2 equivalents of p-toluenesulfonic acid or the mixture of Lumateperone monotosylate and at least about 1 equivalent of p-toluene sulfonic acid is prepared by portionwise or dropwise addition of p-toluenesulfonic acid to the Lumateperone or Lumateperone monotosylate.

14. A process according to claim 6, further comprising combining the crystalline form F1 of Lumateperone ditosylate with at least one pharmaceutically acceptable excipient to form a pharmaceutical composition.

15. A crystalline form of Lumateperone ditosylate obtainable by the process of claim 6.

16. A pharmaceutical composition comprising the solid state forms of Lumateperone ditosylate according to claim 1.

17. A process for preparation of a pharmaceutical composition according to claim 16 comprising combining the solid state forms of Lumateperone ditosylate with at least one pharmaceutically acceptable excipient.

18. A method of treating one or more of: schizophrenia, bipolar disorder, depression, sleep and behavioral disturbance in dementia, autism, and other neuropsychiatric disorders, comprising administering a therapeutically effective amount of the crystalline form of Lumateperone ditosylate according to claim 1 to a patient in need thereof.

19. A method of treating one or more of: schizophrenia, bipolar disorder, depression, sleep and behavioral disturbance in dementia, autism, and other neuropsychiatric disorders, comprising administering a therapeutically effective amount of pharmaceutical composition according to claim 16 to a patient in need thereof.

20. The solid state form of lumateperone ditosylate of claim 1, designated form F1, which contains 20% (w/w) or less of any solid state forms of lumateperone tosylate or lumateperone ditosylate.

21. The solid state form of lumateperone ditosylate of claim 1, designated form F1, which contains 10% (w/w) or less of any solid state forms of lumateperone tosylate or lumateperone ditosylate.

22. The solid state form of lumateperone ditosylate of claim 1, designated form F1, which contains 5% (w/w) or less of any solid state forms of lumateperone tosylate or lumateperone ditosylate.

23. The solid state form of lumateperone ditosylate of claim 1, designated form F1, which contains 2% (w/w) or less of any solid state forms of lumateperone tosylate or lumateperone ditosylate.

24. The solid state form of lumateperone ditosylate of claim 1, designated form F1, which contains 1% (w/w) or less of any solid state forms of lumateperone tosylate or lumateperone ditosylate.

25. The solid state form of lumateperone ditosylate of claim 1, designated form F1, which is substantially free of form A of lumateperone tosylate.

26. The solid state form of lumateperone ditosylate of claim 1, designated form F1, which contains 20% (w/w) or less of form A of lumateperone tosylate.

27. The solid state form of lumateperone ditosylate of claim 1, designated form F1, which contains 10% (w/w) or less of form A of lumateperone tosylate.

28. The solid state form of lumateperone ditosylate of claim 1, designated form F1, which contains 5% (w/w) or less of form A of lumateperone tosylate.

29. The solid state form of lumateperone ditosylate of claim 1, designated form F1, which contains 2% (w/w) or less of form A of lumateperone tosylate.

30. The solid state form of lumateperone ditosylate of claim 1, designated form F1, which contains 1% (w/w) or less of form A of lumateperone tosylate.

31. The process of claim 6, wherein the form F1 is substantially free of any other form of lumateperone tosylate or lumateperone ditosylate.

32. The process of claim 6, wherein the form F1 is substantially free of form A of lumateperone tosylate.

33. The process according to claim 6, wherein
   the solvent system in step (a) comprises one or more of $C_3$-$C_8$ ethers, $C_4$ to $C_{10}$ cyclic ethers, $C_3$-$C_8$ ketones, $C_1$-$C_4$ alcohols, $C_3$-$C_8$ esters, $C_2$-$C_7$ alkyl acetates, or mixtures thereof; and the anti-solvent in step (e) is $C_4$-$C_8$ ethers, $C_3$-$C_8$ alkanes, or $C_5$-$C_{10}$ cycloalkanes.

\* \* \* \* \*